United States Patent [19]

Hayashi et al.

[11] Patent Number: 5,460,943
[45] Date of Patent: Oct. 24, 1995

[54] METHOD OF ASSAY OF ENZYMATIC ACTIVITY

[75] Inventors: Hidechika Hayashi; Yoshihiko Umegae, both of Yokohama; Yukio Mitsuhisa, Ebina, all of Japan

[73] Assignee: Tosoh Corporation, Tokyo, Japan

[21] Appl. No.: 900,286

[22] Filed: Jun. 18, 1992

[30] Foreign Application Priority Data

Jun. 18, 1991 [JP] Japan ................................. 3-146301

[51] Int. Cl.⁶ .................................................. G01N 33/573
[52] U.S. Cl. ........................ 435/7.4; 435/6; 435/7.9;
435/183; 435/967; 435/968; 436/164; 436/172;
436/536; 436/537; 436/805
[58] Field of Search .............................. 356/320, 407,
356/408; 435/6, 7.9, 7.92, 7.93, 7.94, 7.95,
968, 21, 967, 7.4, 4, 18, 183, 196, 207;
436/164, 172, 501, 536, 537, 538, 539,
800, 805

[56] References Cited

U.S. PATENT DOCUMENTS

| | | | |
|---|---|---|---|
| 3,741,876 | 6/1973 | Guilbault, et al. | 435/4 |
| 4,617,261 | 10/1986 | Sheldon III, et al. | 435/6 |
| 4,824,778 | 4/1989 | Nagai et al. | 436/516 |
| 4,954,435 | 9/1990 | Krayth | 436/518 |
| 5,143,825 | 9/1992 | Chacko et al. | 435/968 |

FOREIGN PATENT DOCUMENTS

| | | |
|---|---|---|
| 393326B | 9/1991 | Austria . |
| 0216177 | 4/1987 | European Pat. Off. . |
| 3617946 | 12/1986 | Germany . |

*Primary Examiner*—David Saunders
*Assistant Examiner*—Christopher L. Chin
*Attorney, Agent, or Firm*—Sughrue, Mion, Zinn, Macpeak & Seas

[57] ABSTRACT

Method of assay of enzymatic activity, including projecting excitation light to a sample containing an enzyme, a substrate which forms a product by action of the enzyme, and a reference substance which is insensitive to the action of the enzyme but emits fluorescence; obtaining a first measured value of fluorescence intensity of the sample at a first wavelength region which includes fluorescence emitted by the substrate or the product at least, obtaining a second measured value of fluorescence intensity at a second wavelength region which is different from the first wavelength region for the first measured value and includes fluorescence emitted by the reference substance; and assaying the enzymatic activity from the ratio of the first measured value to the second measured value and apparatus for performing the method. The method assures high accuracy and high sensitivity of measurement in enzyme labeled immunoassay and enzyme labeled DNA hybridization.

7 Claims, 9 Drawing Sheets

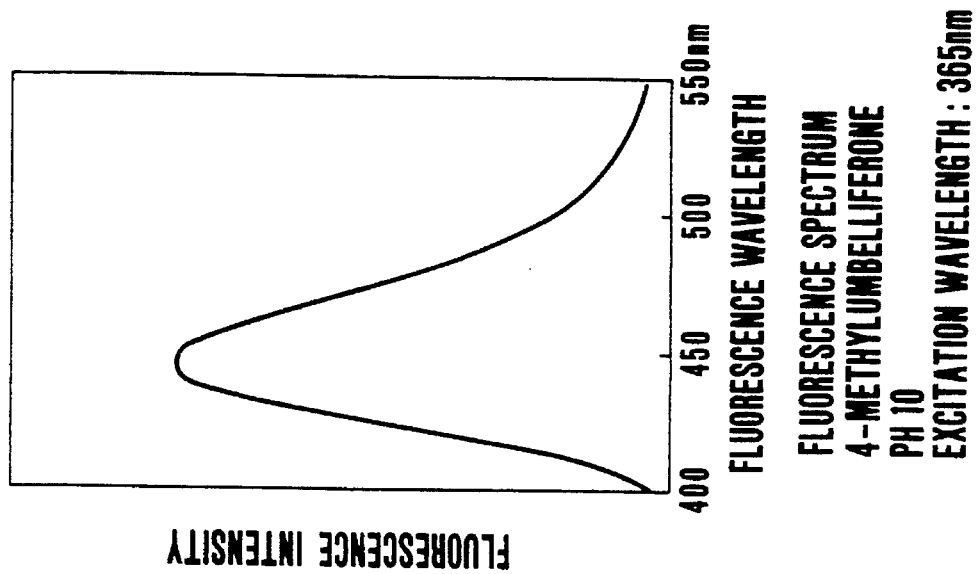
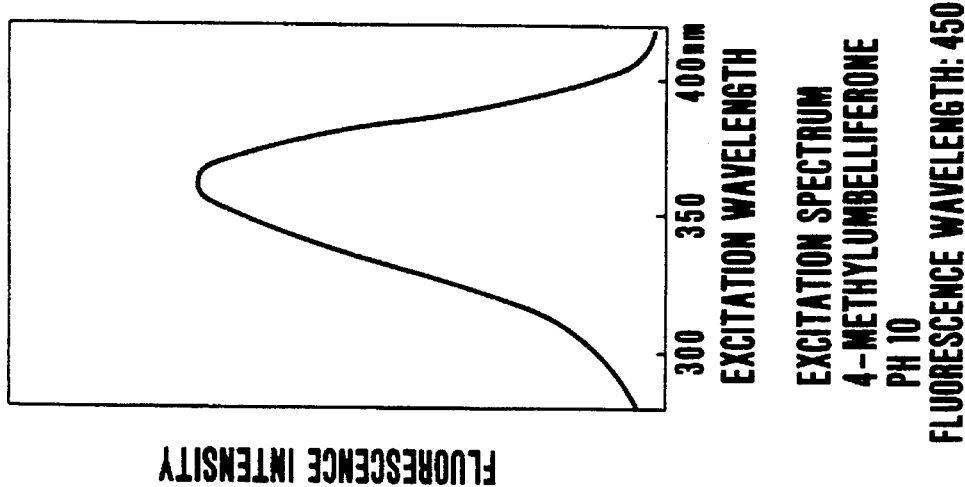

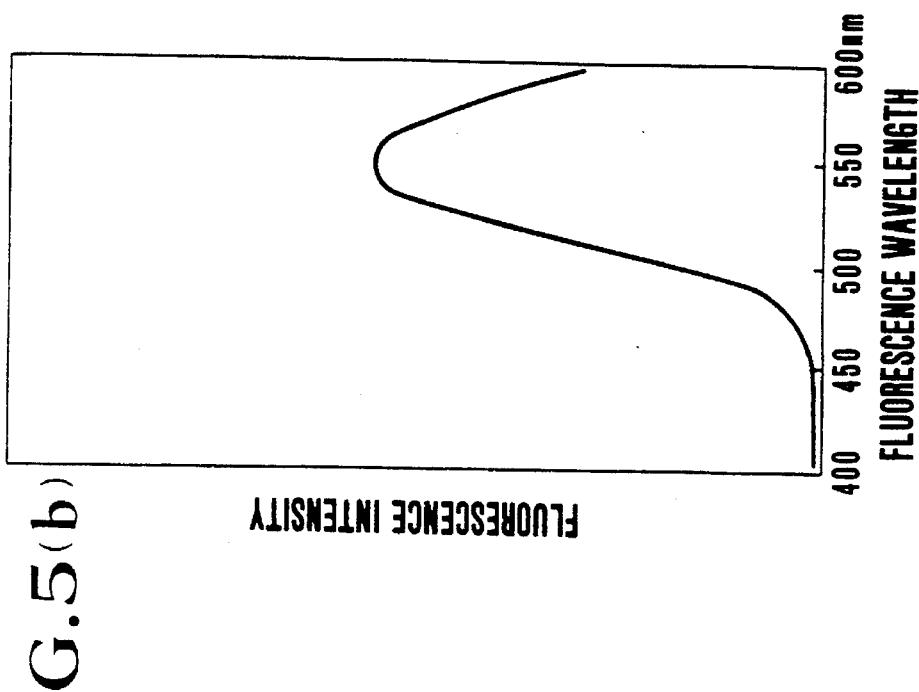
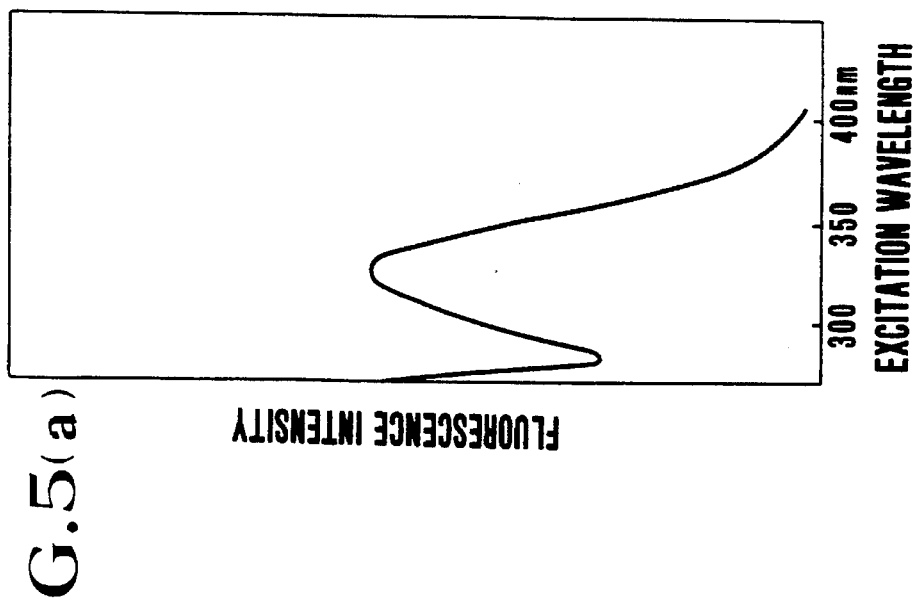
FIG.5(a) EXCITATION SPECTRUM
DANSYLALANINE: 10 μg
FLUORESCENCE WAVELENGTH: 550 nm
FIG.5(b) FLUORESCENCE SPECTRUM
DANSYLALANINE: 10 μg
EXCITATION WAVELENGTH: 325 nm

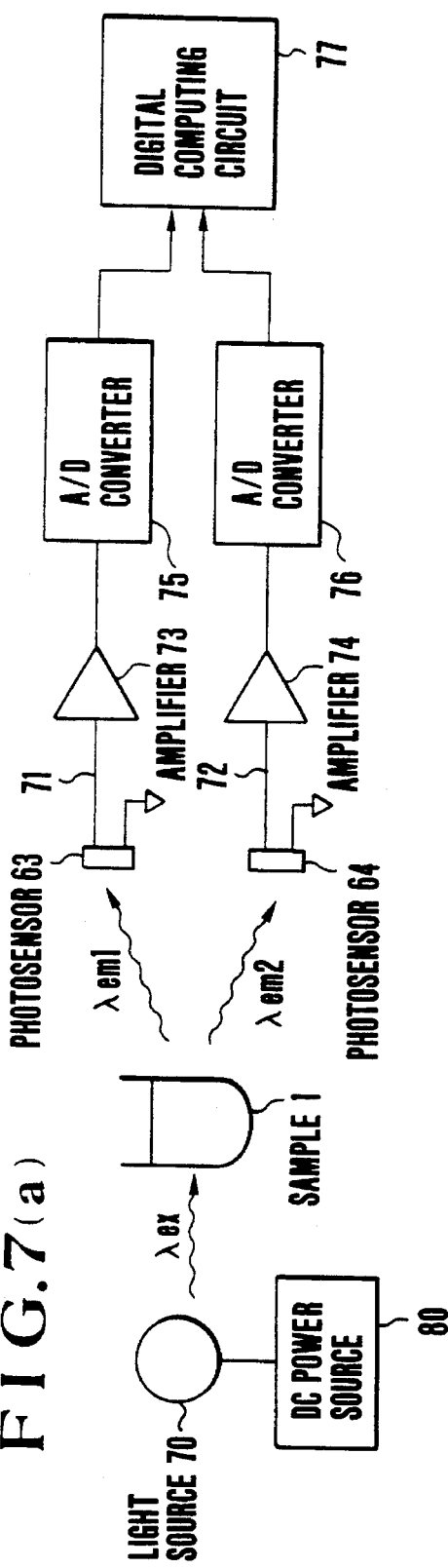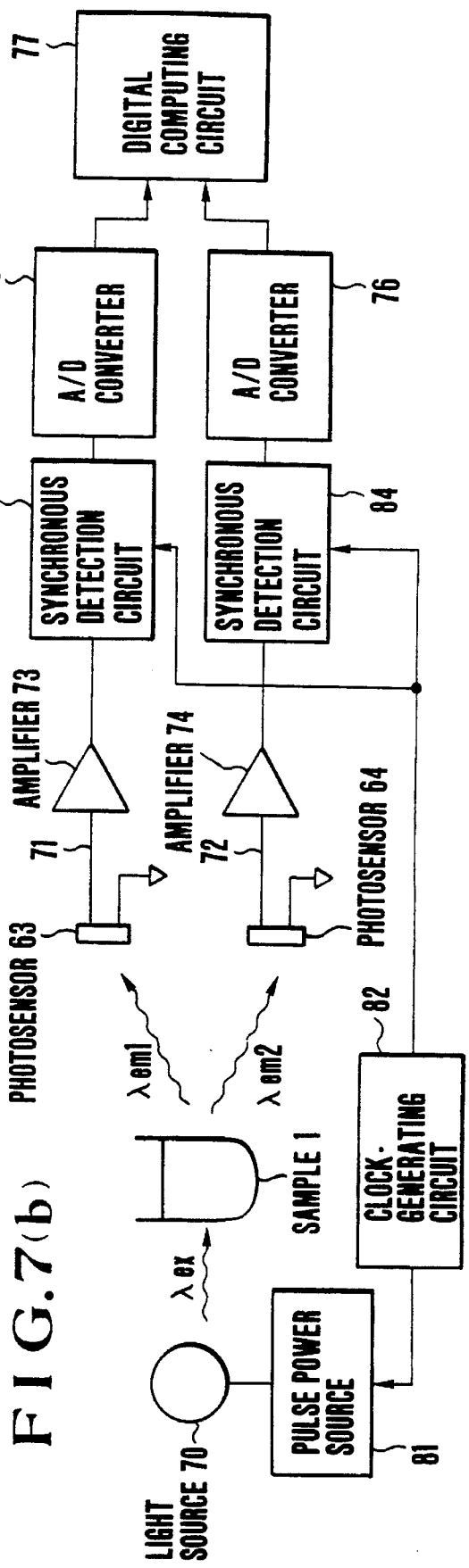

METHOD OF ASSAY OF ENZYMATIC ACTIVITY

BACKGROUND OF THE INVENTION

1. Field of the Invention

The present invention relates to a method of assay of activity of an enzyme employed as a label for immunoassay, etc. based on the detection of fluorescence intensity of a substance having been affected by the enzyme. The present invention also relates to an apparatus used for the assay of the activity of the enzyme.

2. Description of the Related Art

Conventionally known methods for assaying a minute quantity of a biological substance include labeled immunoassay and enzyme-labeled DNA hybridization.

These methods are based on a principle that the biological substance is identified or determined by assaying the activity of an enzyme linked directly or indirectly to an immune complex formed through an immune reaction, or the like, according to detection of the change of the substrate. The known methods include measurement of the change of a light absorption coefficient, measurement of the change of fluorescence intensity, measurement of the change of light emission intensity, of a sample having been affected by enzyme activity, and so forth. From among these methods, the last two methods including measurement of enzyme activity by fluorescence or light emission are advantageous in that a higher sensitivity is achievable in shorter time than in the method which utilizes the light absorption for enzymatic activity assay. The fluorescence method is known to be highly sensitive for assaying enzymatic activity.

Several methods have been reported for quantitative determination of biological substances on the basis of change of fluorescence intensity of a sample. The examples are a method in which the measurement is conducted at a specific point of time after the initiation of an enzymatic reaction and the enzymatic activity is derived from the measured data (a one-point method); a method in which the measurement is conducted at two points of time during the progress of a series of enzymatic reactions and the enzymatic activity is derived from the difference of the two measured data (a two-point method); and a method in which the measurement is conducted nearly continuously and the enzymatic activity was derived from the change rate of the continuously measured data (a rate method).

In recent years, the significance and the importance of quantitative determination of a minute quantity of a substance have been given more attention, in particular, in the fields such as clinical diagnosis. Consequently, the determination of a minute quantity of a biological sample with high precision and high sensitivity has been increasingly required. To meet such requirement, proposals have been made regarding a system which is free from contamination of a sample by another sample, a detecting device for successive measurement of a plurality of samples with high sensitivity, and so forth.

The methods and apparatus of prior arts, which have been proposed or been put into commercial practice for quantitative determination of biological substances with high sensitivity and high precision, have been confronted with limitation in improvement of precision of measurement more than a certain degree because of significant influence of air bubbles in the sample and meniscus of the sample liquid, and so forth. One reason for the above limitation in the improvement is that samples of biological substances to be measured are available only in a minute amount in most cases.

For example, the presence of bubbles in the sample liquid gives a larger value of fluorescence measurement than a value measured in the absence of the bubbles, so that disappearance of the bubbles during the measurement will give, for example, a lower value in a rate method than the real value. On the other hand, the injection of the substrate, which is to be subjected to the reaction with a label enzyme, into a reaction vessel is required to be conducted as quickly as possible in order to treat quickly a number of samples. Further, any adhesion of a liquid drop at the tip of the nozzle needs to be avoided at the completion of dispensing of the sample liquid in order to obtain high accuracy of the volume to be dispensed. However, if the liquid ejection speed is made higher to satisfy the above requirements, the dispensed liquid tends to be foamed more. In the enzyme-labeled immunoassay, an immune reaction complex and an unreacted matter are generally separated from each other (B/F separation) before the substrate injection. If the concentration of surface active agent, which is usually contained in the washing solution, is made higher, more bubbles tend to be formed.

Accordingly, more and more demands have been made for comprehensive investigations to be made to find a novel measurement method which is free from the above problems in principle and enables improvement of the accuracy of the measurement.

Apart from the above problems, a higher detection sensitivity is required in fluorescence measurement. For example, in immunoassay of TSH (thyroid-stimulating hormone), the lower detection limit has conventionally been at a level of about 0.1 µIU/ml, but the limit is now required to be at a level of 0.01 µIU/ml for diagnosis of disease state of an abnormal low value of TSH. Therefore, a higher detection sensitivity is required as well as the suppression of nonspecific reaction of the labeled enzyme. For the improvement of the detection sensitivity, the change of the real measured value has to be distinguished from the variation caused by external disturbance.

SUMMARY OF THE INVENTION

An object of the present invention is to provide a novel method of measurement in enzyme labeled immunoassay and enzyme labeled DNA hybridization, which is less affected by obstructions in improvement of measurement accuracy: such as the adverse effect by the presence of bubbles in the sample, influence of the meniscus, influence of agitation with magnetic particles with a vibrating magnetic field in the reaction vessel for purposes of stirring the sample, influence of variation of light source intensity with time, and so forth, and which enables the measurement with high accuracy, and high sensitivity; and to provide also the apparatus for the method.

Another object of the present invention is to provide a method for the above measurement which is not affected by any variation in the quantity of light projected to the reaction vessel owing to variation in the relative position of the reaction vessel to the light source, and which can achieve high sensitivity of measurement consistently, and to provide also the apparatus for the method.

A further object of the present invention is to provide a novel method for the measurement in enzyme labeled immunoassay and enzyme labeled DNA hybridization, which enables simplification and automation of the substrate dispenser and the sample agitator, which could not be simplified nor automated due to requirements for reducing measurement errors, without lowering the accuracy, and to provide also an apparatus for the method.

The present invention provides a method of assay of enzymatic activity, comprising projecting excitation light to a sample containing an enzyme, a substrate which forms a product by action of the enzyme, and a reference substance which is insensitive to the action of the enzyme but emits fluorescence; obtaining a first measured value of the fluorescence intensity of the sample at a first wavelength region which includes fluorescence emitted by the substrate or the product at least, obtaining a second measured value of the fluorescence intensity at a second wavelength region which is different from the first wavelength region for the first measured value and includes at least the fluorescence emitted by the reference substance; and assaying the enzymatic activity from the ratio of the first measured value to the second measured value.

The apparatus according to the present invention for performing the above method comprises light-projecting means for projecting excitation light to a sample containing a fluorescent substance which increases or decreases by action of an enzyme, and a reference substance which emits fluorescence and is insensitive to the action of the enzyme; first photosensing means for measuring fluorescence intensity of wavelength for a first measured value of fluorescence originating from the fluorescent substance out of the entire fluorescence emitted by the sample; second photosensing means for measuring fluorescence intensity at wavelength for a second measured value of fluorescence originating from the reference substance out of the entire fluorescence emitted by the sample; and computing means for computing the enzyme activity from input of the first measured value and the second measured value.

BRIEF DESCRIPTION OF THE DRAWINGS

FIG. 4(a) shows the excitation spectrum and FIG. 4(b) shows the fluorescence spectrum of 4-methylumbelliferone, which is produced from 4-methylumbelliferyl phosphate by action of alkaline phosphatase.

FIG. 5(a) shows the excitation spectrum and FIG. 5b shows the fluorescence spectrum of dansylalanine as the reference substance.

FIG. 7(a) and FIG. 7(b) illustrate respectively a signal processing in the measurement of the present invention.

DETAILED DESCRIPTION OF THE PREFERRED EMBODIMENT

Figure 1:
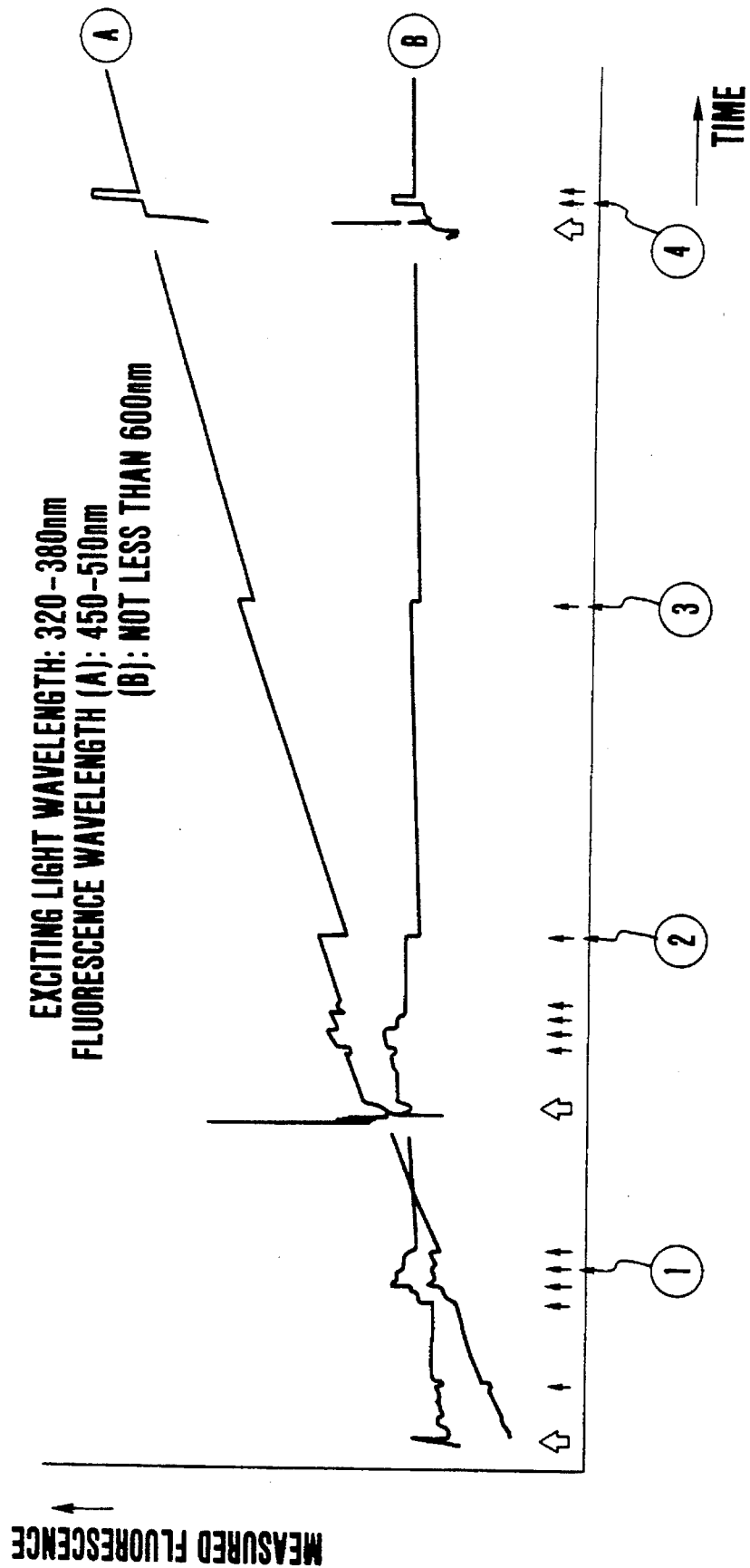
FIG. 1 shows the dependency on time of the first measured value at the first fluorescence wavelength region and the second measured value at the second fluorescence wavelength region which were measured in Example 1.

The enzymatic activity can be assayed according to the change rate relative to time of the ratio derived by dividing a first measured value at a first wavelength region by a second measured value at a second wavelength region in comparison with a calibration curve prepared preliminarily by use of known samples. The change rate relative to time of the fluorescence intensity is preferably derived by the aforementioned two-point method, or derived nearly continuously by the aforementioned rate method in which the measurement is conducted nearly continuously to follow the progress of the enzymatic reaction, and therefrom the enzymatic activity is assayed. However, the method is not limited thereto.

The feature of the method of the present invention is explained as below.

It is assumed here that the substrate, the product formed by action of the enzymatic action, and the reference substance are all fluorescent. The case is considered where excitation light is projected to the system containing the substances. In this case, the intensity of the fluorescence emitted from each of the substances is proportional to the concentration of each fluorescent substance, and external disturbance such as bubbles affects all of the measured data. Therefore, the first measured value (FI 1) obtained at the above specified wavelength and the second measured value (FI 2) obtained at another wavelength are respectively shown by the equations below.

$$(FI\ 1) = p \times (k1 \times [\text{Substrate}] + k2 \times [\text{Product}] + k3 \times [\text{Reference}])$$

$$(FI\ 2) = p \times (k4 \times [\text{Substrate}] + k5 \times [\text{Product}] + k6 \times [\text{Reference}])$$

wherein p is a coefficient of the fluorescence variation affecting the entire sample resulting from bubbles and other causes; [Substrate], [Product], and [Reference] are respectively the concentration of the substrate, the product, and the reference substance; and k1 to k6 are proportion coefficients corresponding to the respective wavelengths.

Therefore, the ratio of (FI 1) to (FI 2) in the present invention is shown by Formula (1) below. This formula is transformed to Formula (2) to represent the substrate concentration as a function of the product concentration. Thus the concentration of the product is derived from the concentration of the reference substance and the proportion coefficients k1 to k6.

$$\frac{(FI\ 1)}{(FI\ 2)} = \frac{p \times (k1 \times [\text{Substrate}] + k2 \times [\text{Product}] + k3 \times [\text{Reference}])}{p \times (k4 \times [\text{Substrate}] + k5 \times [\text{Product}] + k6 \times [\text{Reference}])} \quad (1)$$

$$\{k1 \times ([\text{Substrate}]_0 - [\text{Product}]) + k2 \times [\text{Product}] + k3 \times [\text{Reference}]\} \times FI\ 2 = \{k4 \times ([\text{Substrate}]_0 - [\text{Product}]) + k5 \times [\text{Product}] + k6 \times [\text{Reference}]\} \times FI\ 1 \quad (2)$$

where $[\text{Substrate}]_0$ is the initial concentration of the substrate added to the reaction vessel, and is a known value. Thus, it is understood that the influence of the variation of the fluorescence intensity is canceled by taking the ratio of two measured values according to Formula (1) or Formula (2).

The above formulas are shown to describe generally the case where the substrate, the product, and the reference material emit respectively fluorescence by irradiation of excitation light. However, other cases where k1=0, or k1=k4=k5=0 may be selected by selecting the wavelength for the first measured value or for the second measured value, including the case where the coefficient or coefficients are not completely zero but practically can be considered as being zero. The purpose of the present invention is achieved essentially by measuring the fluorescence intensity of the enzymatic reaction product as the one measured value (e.g., the first measured value) and the fluorescence intensity of the reference substance as the other measured value (e.g., the second measured value).

The wavelength of the excitation light in the present invention is selected so as to excite at least one of the substrate and the product, as well as the reference substance.

The fluorescence wavelength for obtaining the first measured value (hereinafter referred to as the "first fluorescence wavelength") is selected from the wavelength range of the fluorescence emitted from the substrate or the product, and the fluorescence wavelength for obtaining the second measured value (hereinafter referred to as the "second fluorescence wavelength") is selected from the wavelength range of the fluorescence emitted from the reference substance. The wavelength herein covers a required wavelength region.

The wavelength of the excitation light and the first fluorescence wavelength are selected such that the change of the fluorescence characteristics caused by the change of the substrate into the product is reflected in the measured fluorescence intensity.

It is preferable that the reference substance contained in the sample has a fluorescence peak wavelength departed at least 50 nm from a fluorescence peak wavelength of the substrate and/or the product formed by the substrate.

Thus when the respective fluorescences of the product and the reference substance are measured, it is preferable to use a reference substance having a fluorescence peak wavelength departed at least 50 nm from the fluorescence peak wavelength of the product.

Also when the fluorescences of the substrate and the reference substance are measured, it is preferable to use a reference substance having a fluorescence peak wavelength departed at least 50 nm from the fluorescence peak wavelength of the substrate.

As an example for the combination, 4 MU (fluorescence wavelength 450 nm) produced from 4 MUP by alkaline phosphatase is used in combination with dansylhydrazine (fluorescence wavelength 500 nm).

With the combinations mentioned above it is possible to minimize the measurement error caused by the fluorescence peaks and to obtain a high degree of accuracy of the measurement. However it is more preferable to use a reference substance having a fluorescence peak wavelength departed at least 50 nm from the fluorescence peak wavelengths of the substrate and the product. This combination enables a high degree of accuracy of measurement in all cases where the fluorescence of the substrate is measured and where fluorescence of the product is measured.

The enzyme includes a free enzyme of natural origin, an enzyme linked to a free antigen, antibody, or DNA, an enzyme bonded indirectly to an inner wall of a small container or a surface of a sheet as at obtained by enzyme labeled immunoassay or enzyme labeled DNA hybridization, and the like.

The labeled enzyme for enzyme labeled immunoassay and enzyme labeled DNA hybridization is exemplified typically by alkaline phosphatase, β-galactosidase, and the like. The substrate which changes its fluorescence intensity by the action of the alkaline phosphatase is exemplified by 4-methylumbelliferyl phosphate. This substrate is converted to 4-methylumbelliferone by the action of the above enzyme. The substrate which changes its fluorescence intensity by the action of the β-galactosidase is exemplified by 4-methylumbelliferyl galactoside. This substrate is converted to 4-methylumbelliferone by the action of the above enzyme. For example, when excitation light of wavelength of 365 nm (see FIG. 4(a)) is projected to the above product (4-methylumbelliferone) in alkaline medium (pH 10), the 4-methylumbelliferone emits fluorescence having maximum intensity at about 450 nm (see FIG. 4(b)), while the fluorescence emitted by 4-methylumbelliferyl phosphate or 4-methylumbelliferyl galactoside is negligible. Accordingly, the fluorescence intensity emitted by the product can be measured by projecting the excitation light of 365 nm to a sample, and measuring fluorescence at the wavelength around 450 nm from the entire fluorescence of the sample.

The reference substance, which is characteristic to the present invention, to be added to a sample containing the substrate and the product as mentioned above is selected from the substances which emit fluorescence in a spectrum pattern different from that of the above fluorescence spectrum which is changed by the enzymatic action.

In the case of the above typically exemplified 4-methylumbelliferone, the reference substance is preferably selected from the substances which emit fluorescence, for example, of wavelength of 500 nm or more on receiving excitation light of 365 nm. The examples of such reference substances are shown below.

| (Structural formula) | $(Ex^{max})$ nm | $(Em^{max})$ nm |
|---|---|---|
| 1) Dansyl compounds: (Example) Dansylsulfonic acid | 325 | 550 |
| Dansyl chloride | 325 | 550 |

-continued

| (Structural formula) | (Ex^max) nm | (Em^max) nm |
|---|---|---|
| Dansylamino acids (Example) Dansyl-L-alanine | 325 | 550 |
| Dansylhydrazine | 340 | 525 |
| 2) 4-Dimethylamino-1-naphthoylnitrile | 350 | 530 |
| 3) N-(1-anilinonaphthyl)-4-maleimide | 350 | 530 |
| 4) 7-Benzylamino-4-nitrobenz-2-oxa-1,3-diazole (R = H) 7-(p-Methoxy-benzylamino)-4-nitrobenz-2-oxa-1,3-diazole (R = OCH₃) | 340 or 458 | 530 |

The above substances have the maxima of the excitation spectra not at 365 nm. However, the dansyl-L-alanine shown above has a breadth in its excitation spectrum as shown in FIG. 5(a). Therefore, projection of excitation light of 365 nm causes the emission of fluorescence having the maximum at about 550 nm (FIG. 5(b)).

In the case where the enzymatic reaction product is 4-methylumbelliferone and the reference substance used is dansyl-L-alanine, the fluorescence spectra of the both substances partly overlap with each other (FIG. 4(b) and FIG. 5(b)). If the light of about 450 nm is selected as the first fluorescence wavelength, the light includes a slight portion of the fluorescence of the reference substance. However, the rate of change with time of the ratio of the first measured value obtained at the first fluorescence wavelength to the second measured value obtained at the wavelength of 500 nm or more is not affected thereby, which is the characteristic of the present invention.

Further in the aforementioned case, the second measured value obtained at the second fluorescence wavelength include a portion of the fluorescence of 4-methlumbelliferone. However, the effect of the present invention is appropriately exhibited by selecting the second fluorescence wavelength and the concentration of the reference substance such that the influence of the 4-methylumbelliferone is not large. Specifically, for example, in practicing the above case, the concentration of the reference substance to be incorporated in the sample is preferably selected within the range to give sufficient fluorescence in intensity at the second fluorescence wavelength and not to cause excessively large absorption of the excitation light by the reference substance. Generally the absorption ratio should not be more than 50%. In the case where the fluorescence spectrum of the substrate or the product overlaps with the excitation spectrum of the reference substance, the fluorescence emitted by the substrate or the product is re-absorbed by the reference substance. In this case, the concentration of the reference substance is preferably selected within the range that the ratio of the re-absorption is not large, generally not more than 50%.

Any sample may be subjected to the assay of the present invention, provided that the enzyme labeled immunoassay or the enzyme labeled DNA hybridization is applicable to the sample. In most cases, the sample in a small container having a cup shape is brought into an assay apparatus.

The apparatus for the assay of enzymatic activity of the present invention includes a light-projecting means for projecting excitation light to a sample containing a fluorescent substance which increases or decreases by action of an enzyme, and a reference substance which emits fluorescence and is insensitive to the action of the enzyme; a first photosensor means for measuring fluorescence intensity of wavelength for a first measured value of fluorescence originating from the fluorescent substance out of the entire fluorescence emitted by the sample; a second photosensor means for measuring fluorescence intensity at wavelength for a second measured value of fluorescence originating from the reference substance out of the entire fluorescence emitted by the sample; and a computing means for computing the enzyme activity from input of the first measured value and the second measured value.

The aforementioned light-projecting means is generally an optical system constituted by suitably combining a light source, a lens, a filter, a mirror, a condenser lens, etc. The light source is preferably of a flasher type, since it enables elimination of the influence of external disturbing light, etc. from the signal obtained from the photosensor by synchronous wave detection at the light-receiving side to take out exclusively the fluorescence component emitted by the sample, thus enabling more reliable detection of fluorescence intensity. As the flashing light source, a discharge lamp or a fluorescence lamp which flashes at a frequency ranging from tens of Hz to several hundred Hz is advantageous rather than a lamp flashed by a mechanical chopper in view of its durability in long time of continuous operation. The power source may be an AC source or a pulse source operated at the aforementioned frequency, or a high frequency AC source of several kHz to several ten kHz which is switched on and off at the above frequency.

The photosensor means of the apparatus for enzymatic activity assay includes a first photosensor means and a second photosensor means. Each of the photosensor means is constituted by combining a light-receiving optical system including a mirror, a condenser lens, a filter, a photosensor such as a photodiode and a photomultiplier, and an electric circuit such as an amplifier. As described above, if a light source-flashing means is employed, a wave detector is also used which detects synchronously electric signals from a photosensor by utilizing clock signals for flashing the light source such as a fluorescence lamp.

The apparatus for assay of enzymatic activity of the present invention may be of a system in which the fluorescence emitted from the sample is detected in a direction opposite to the projection of the excitation light to the sample, or otherwise may be of a system in which the direction of the fluorescence detection is perpendicular to the projection of the excitation light. For efficient continuous assay of enzymatic activity of a number of samples, an embodiment of a top-top type is preferred in which the optical path of the light-receiving system is superposed on the optical path of the light-projection system. In an example, a dichroic mirror or the like is placed in an optical path of a light-projecting system to reflect the light from the light source downward, and the fluorescence emitted upward by the sample is divided into the light components of the first fluorescence wavelength and the second fluorescence wavelength with a filter, a half-mirror, or a dichroic mirror placed in the optical path of the light receiving system. Thus, the respective light components can be detected by separate photosensors. In particular, the use of a dichroic mirror is advantageous in that excitation light and fluorescence are effectively utilized with reduced loss by selecting the property thereof in accordance with the wavelength of the excitation light and the fluorescence.

The light source, the photosensor, the filter, etc. are placed in suitable positions in accordance with the properties of the employed elements such as a dichroic mirror.

Figure 6A:
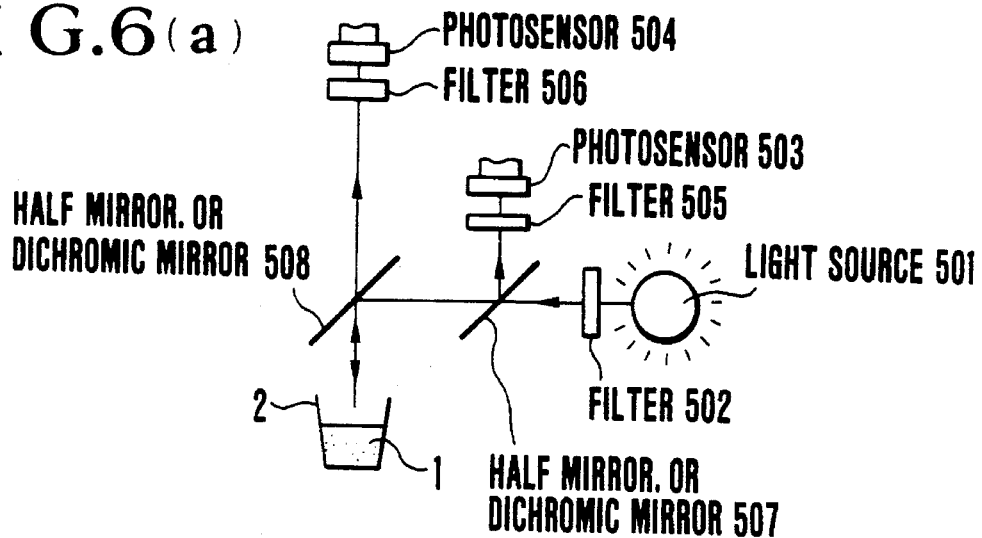
FIG. 6(a) to FIG. 6(c) illustrate respectively an optical measurement system constituting an enzyme labeled immunoassay apparatus of the present invention.
Figure 6B:
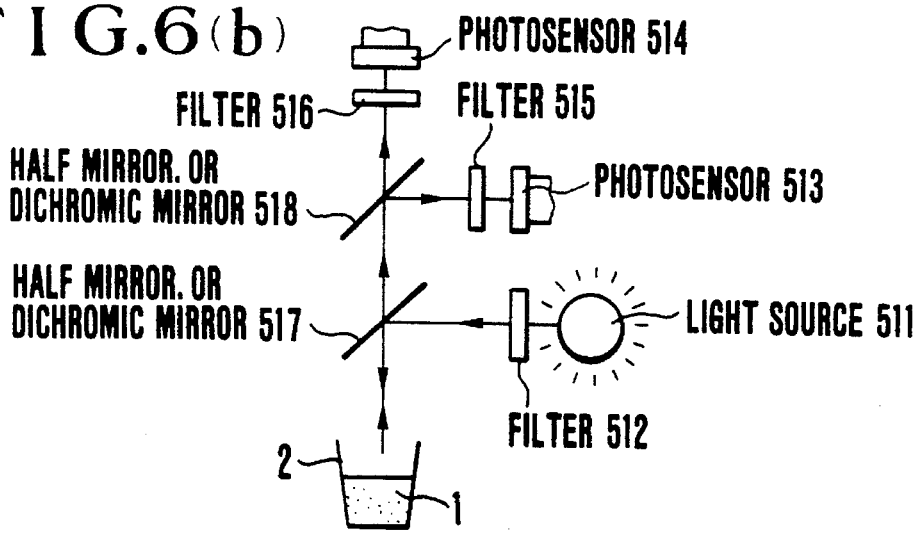
Figure 6C:
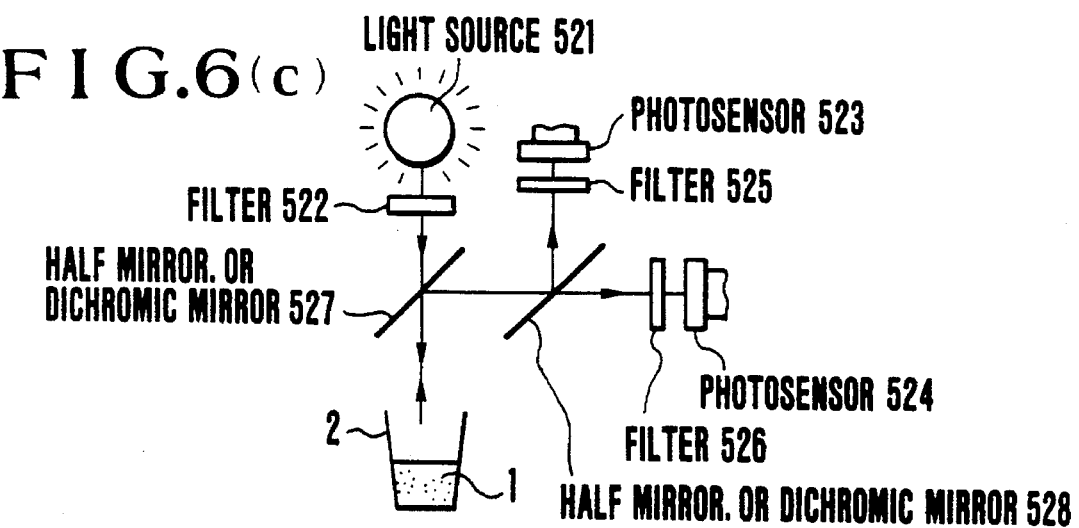
Figure 8A:
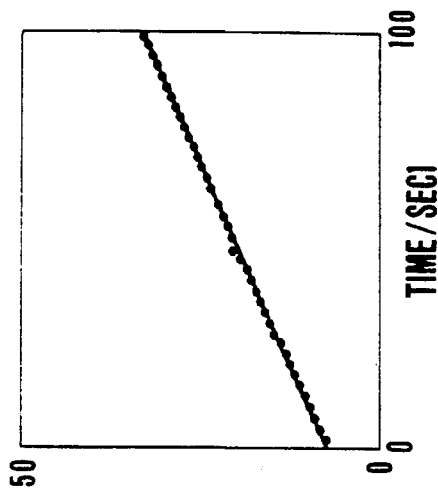
In FIG. 8, (a) and (b) show the change of fluorescence intensity of a liquid sample, when alkaline phosphatase is added thereto, as calculated according to a conventional method; and (A) and (B) show the same change but calculated according to the method of the present invention.
Figure 8B:
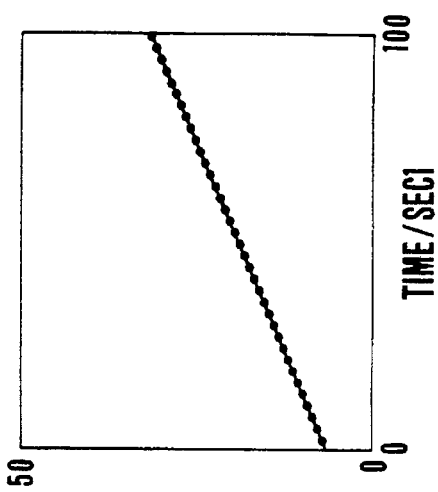
Figure 8A:
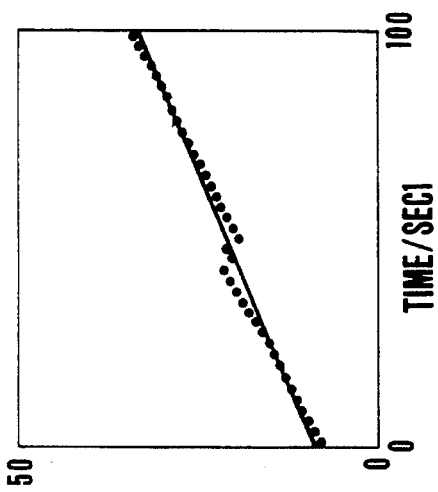
Figure 8B:
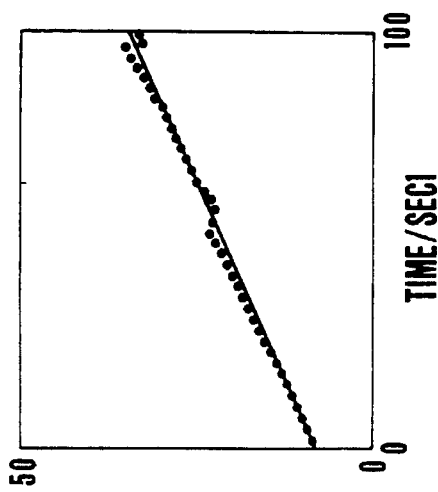
Figure 9C:
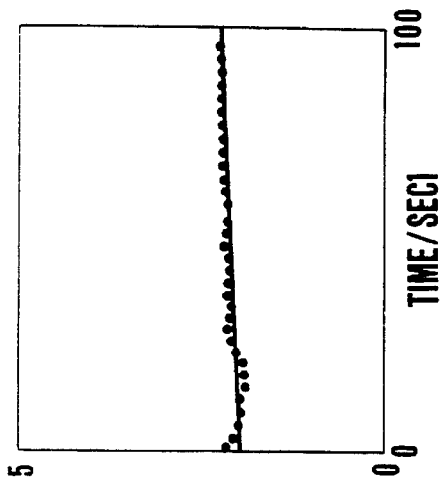
In FIG. 9, (c) and (d) show the change of fluorescence intensity of a liquid sample, when alkaline phosphatase is not added thereto, as calculated according to a conventional method; and (C) and (D) show the same change but calculated according to the method of the present invention.
Figure 9D:
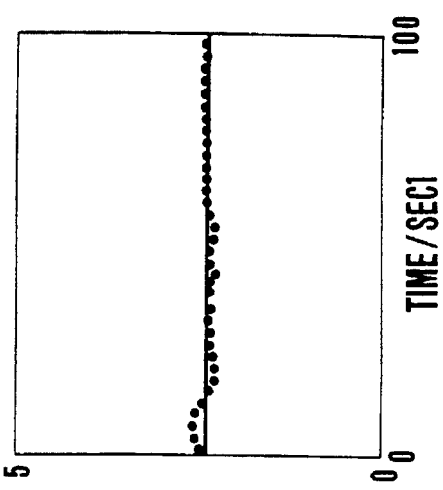
Figure 9C:
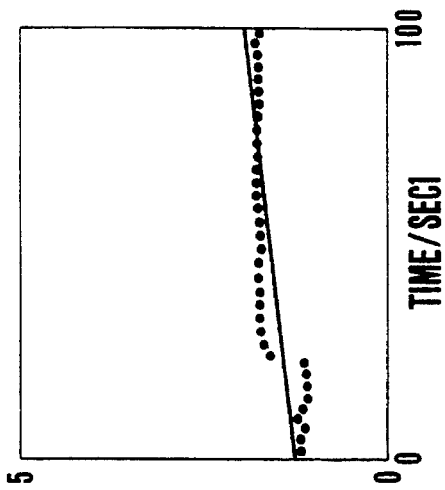
Figure 9D:
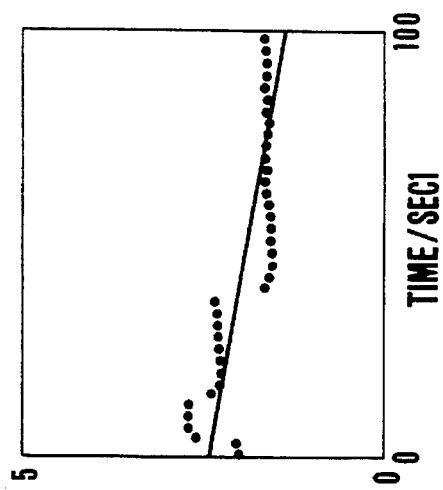

FIG. 6(a) to FIG. 6(c) illustrate roughly examples of embodiments of the optical system of the top-top type as mentioned above. The light from a light source 501 is projected through a half-mirror or a dichroic mirror 507, 508 to a sample 1 in a sample container 2. Fluorescence emitted by the sample is introduced through filters 505, 506 to photosensors 503, 504. In FIG. 6(b) and FIG. 6(c), the symbol numbers correspond respectively to the ones in FIG. 6(a) provided that the numeral 10 or 20 is added thereto, respectively.

In the division processing of the computing device according to the present invention, a first electrical signal obtained by a first light-receiving system and a second electrical signal obtained by a second light-receiving system may be processed in an analog manner, or otherwise the above electrical signals may be once converted by A/D converters to digital signals and then be processed by a digital computing circuit such as a digital computer.

FIG. 7 illustrates schematically a signal processing system of a measuring apparatus having the above-described constitution. FIG. 7(a) illustrates an example employing a light source 70 continuously lighted by a DC power source 80. FIG. 7(b) illustrates another example employing a light source 70 flashed by a pulse source 81. The light introduced to photosensors 63, 64 is amplified as electrical signals 71, 72 by amplifiers 73, 74, converted to digital signals by A/D converters 75, 76, and then processed by a digital computing circuit 77 such as a computer to calculate, for example, the change rate as a function of time and to obtain division quotient.

In FIG. 7(b), a clock-generating circuit 82 synchronizes the pulse source 81 with a synchronous wave detecting circuits 83, 84.

Naturally, the electrical signals 71, 72 may be inputted to an analog division circuit. The outputs therefrom being converted to digital signals by A/D converters, and being processed by a digital computing circuit such as a computer to calculate the above change rate as a function of time.

The present invention is described in more detail by reference to examples shown in the drawings.

EXAMPLE 1

Figure 3:
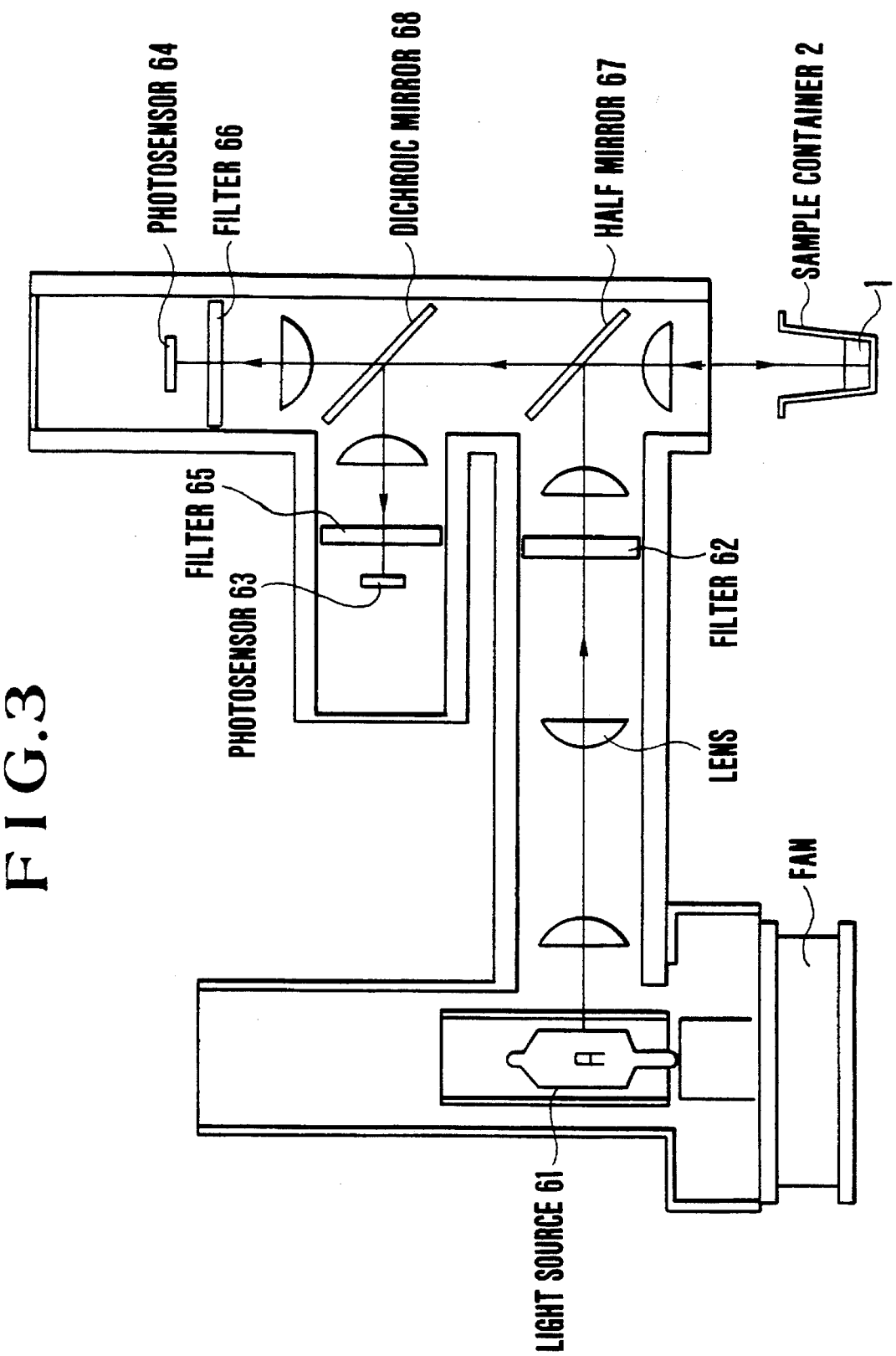
FIG. 3 illustrates an outline of the fluorescence detector employed in Examples of the present invention.

FIG. 3 illustrates an example of a measuring apparatus for the assay of the present invention (an embodiment having a top-top type of optical system). In the drawing, a cup-shaped sample container 2 (top end diameter: 10 mm, volume: 1 ml) holds a small amount—several tens to hundreds μl—of a sample liquid 1. The sample in the container passes through processes of a substrate dispense and an enzyme reaction, which are not shown in the drawing, and transferred to the place for fluorescence detection. FIG. 3 illustrates a state that the sample container 1 is set in a measurement position. The product formed from the substrate was a product from 4-methylumbelliferyl phosphate by action of alkaline phosphatase, the product being 4-methylumbelliferone having fluorescence characteristics shown in FIG. 4(a) and FIG. 4(b), and the reference substance was dansyl-L-alanine having fluorescence characteristics shown in FIG. 5(a) and FIG. 5(b).

A light source 61 emits excitation light of the light-projecting optical system. The light passed through a filter 62 which allows the light in the wavelength range of from 320 nm to 380 nm to transmit, and then the light is reflected by a half-mirror 67 to be projected downward as the excitation light to the sample 1 in the sample container 2.

Fluorescence caused by the irradiation of the exciting light and emitted by the sample liquid 1 passes through the half-mirror 67 and is separated by the dichroic mirror 68 into the light including the first fluorescence wavelength and the light including the second fluorescence wavelength. The dichroic mirror 68 is designed to have a property that it transmits light having wavelength of 530 nm or longer but reflects light having wavelength of from 420 nm to 530 nm.

The light of the first fluorescence wavelength separated by the dichroic mirror 68 is introduced to a filter 65 which transmits light of from 450 nm to 510 nm, and selected wavelength of light is introduced to a photosensor 63. On the other hand, the light of the second fluorescence wavelength proceeds upward and is introduced to a filter 66 which transmits light of 600 nm or longer, and the selected wavelength of light is introduced to a photosensor 64.

With the measuring apparatus having the constitution described above, the fluorescence of a sample liquid was measured which contained a biological substance labeled with alkaline phosphatase, 4-methylumbelliferyl phosphate as the substrate, and dansyl-L-alanine as the reference substance mixedly. The alkaline phosphatase was used in an appropriate quantity, 4-methylumbelliferyl phosphate was at a concentration of 1 mM, and dansyl-L-alanine was at a concentration of 100 μg/ml.

Figure 2:
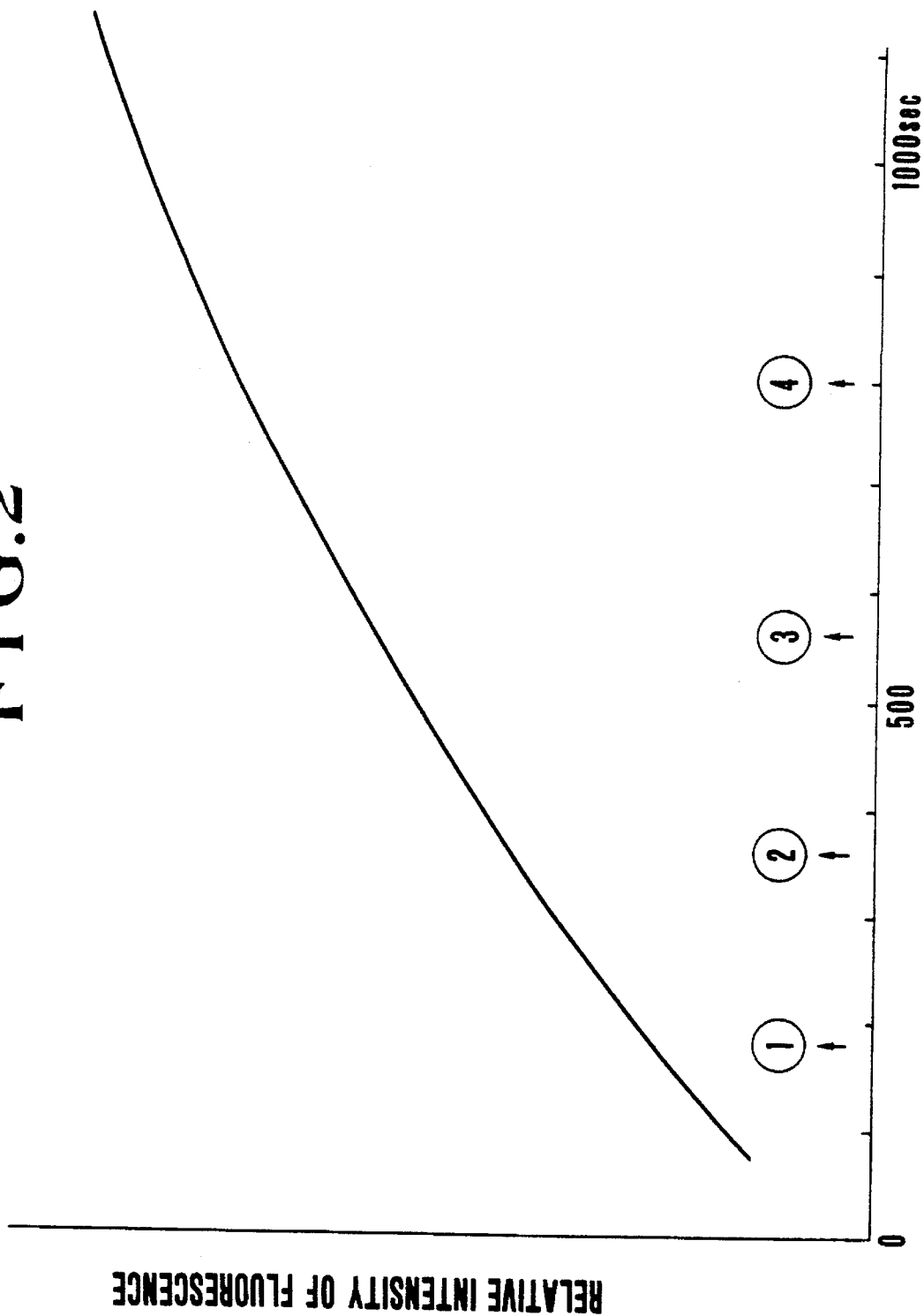
FIG. 2 shows the dependency on time of the relative fluorescence intensity derived by dividing the first measured value by the second measured value.

The measured value A of the first fluorescence wavelength and the measured value B of the second fluorescence wavelength detected thereby are shown in FIG. 1. The ratio of the first measured value at the first fluorescence wavelength to the second measured value at the second fluorescence wavelength (relative fluorescence intensity) is shown as a function of time in FIG. 2. In FIG. 1 and FIG. 2, the denotations (1) to (4) shows the time when air is blown artificially into the sample liquid and the bubbles formed thereby disappeared or moved away, causing changes of the measured fluorescence intensity.

From the comparison of FIG. 1 with FIG. 2, it is understood that the fluorescence intensity changes greatly by blow of air but the ratio of the first measured fluorescence to the second measured fluorescence is not affected by the presence of the air bubbles. Thus it is confirmed that the present invention enables precise detection of the change of fluorescence intensity emitted by a fluorescent substance without the adverse effect of the presence of air bubbles in the sample.

EXAMPLE 2

The experiment below was conducted in order to compare the result of the measurement obtained by the method of the present invention with a conventional method.

An apparatus AIA-1200 (made by Tosoh Corporation) was employed which has the same constitution as the one employed in Example 1.

A solution was preliminarily prepared by dissolving 26 mg of 4-methylumbelliferyl phosphate in 100 ml of an aqueous solution containing 4.5 g of 2-amino-2-methyl-1-propanol and further dissolving therein 0.1 mg/ml of dansyl-L-alanine (10 mg to 100 ml of the substrate solution).

Into a sample container having several magnetic particles (about 1.5 mm in diameter) for stirring, 50 µl of alkaline phosphatase was dispensed manually by a pipetter, and further thereto 200 µl of the above, preliminarily prepared solution was dispensed manually by a pipetter.

The container was immediately placed below the detector. The fluorescence intensity was measured every 2 seconds, beginning several seconds after the addition of the solution for 100 seconds at the first and the second wavelengths. The rate was derived according to the calculation formula (3) by a least square method (Test Nos. 1 to 10). The results are shown in Table 1. Throughout the measurement, the magnetic particles were moved in reciprocation by magnetic vibration. In the experiments of Test Nos. 1 and 9, air was introduced into the liquid in the container just before the detection operation.

$$[(Sig(4MU)-Sig(4MU_0))] / [(ref(DLA)-ref(DLA_0))] \quad (3)$$

where $Sig(4MU)$ is a measured value of fluorescence intensity at the first wavelength (substantially the fluorescence intensity of 4-methylumbelliferone); $Sig(4MU_0)$ is a measured value for the empty container at the first wavelength; $ref(DLA_0)$ is a measured value of fluorescence intensity at the second wavelength (substantially the fluorescence intensity of the reference substance); and $ref(DLA_0)$ is a measured value for the empty container at the second wavelength.

The same tests were conducted in the same manner as above except that the alkaline phosphatase was not added, and the fluorescence intensity was measured and the rate was calculated (Test Nos. 11 to 19). The results are shown in Table 2. In the experiments of Test Nos. 13 and 15, air was introduced into the liquid in the container just before the detection operation. In the experiments, the agitation magnetic beads used had been obtained from a commercial immunodiagnostic reagent (E Test "TOSOH" made by Tosoh Corporation). Although the beads were washed sufficiently before the use, a slight amount of alkaline phosphatase was believed to remain adhered to the surface thereof.

For comparison, for the respective cases where the alkaline phosphatase is added and not added, the rates were calculated from the measured fluorescence intensity only at the first wavelength according to a conventional method by use of the formula (4) by a least square method (No. 1 to No. 10, and No. 11 to No. 19). The result are show in Table 1 and Table 2.

$$[\{Sig(4MU)-Sig(4MU_0)\}/ref(UV)] \times 50 \quad (4)$$

where $Sig(4MU)$ and $Sig(4MU_0)$ mean the same as in the formula (3), and the term "ref(UV)" is for canceling the variation of the source light with time by dividing the measured value by the light intensity and the term (×50) is a factor for convenience to facilitate the comparison of the data with the measured value of the present invention.

TABLE 1

| No. | $R_{old}$ (/sec) | $R_{new}$ (/sec) |
|---|---|---|
| 1 | 0.232 | 0.256 |
| 2 | 0.267 | 0.257 |
| 3 | 0.276 | 0.259 |
| 4 | 0.277 | 0.256 |
| 5 | 0.280 | 0.256 |
| 6 | 0.270 | 0.248 |
| 7 | 0.236 | 0.224 |
| 8 | 0.291 | 0.250 |
| 9 | 0.267 | 0.253 |
| 10 | 0.285 | 0.252 |
| Average | 0.268 | 0.251 |
| CV | 6.9% | 3.8% |

Note:
$R_{old}$: Measured values by a conventional method
$R_{new}$: Measured values by the method of the invention
CV: Coefficient of variation

TABLE 2

| No. | $R_{old}$ (/sec) | $R_{new}$ (/sec) |
|---|---|---|
| 11 | $0.120 \times 10^{-3}$ | $0.157 \times 10^{-3}$ |
| 12 | $0.098 \times 10^{-3}$ | $0.082 \times 10^{-3}$ |
| 13 | $0.733 \times 10^{-3}$ | $0.315 \times 10^{-3}$ |
| 14 | $0.099 \times 10^{-3}$ | $0.129 \times 10^{-3}$ |
| 15 | $-1.05 \times 10^{-3}$ | $0.023 \times 10^{-3}$ |
| 16 | $-0.112 \times 10^{-3}$ | $0.119 \times 10^{-3}$ |
| 17 | $0.131 \times 10^{-3}$ | $0.134 \times 10^{-3}$ |
| 18 | $0.175 \times 10^{-3}$ | $0.026 \times 10^{-3}$ |
| 19 | $-0.289 \times 10^{-3}$ | $0.038 \times 10^{-3}$ |
| Average | $-0.0105 \times 10^{-3}$ | $0.144 \times 10^{-3}$ |
| SD | $0.0449 \times 10^{-3}$ | $0.0998 \times 10^{-3}$ |

Note:
$R_{old}$: Measured values by a conventional method
$R_{new}$: Measured values by the method of the invention
SD: Standard deviation From the results in Table 1, the method of the present invention is confirmed to give measurement results with a smaller coefficient of variation (CV value) and higher accuracy than the conventional method. From the results in Table 2, the method of the present invention is confirmed to give much smaller standard deviations (SD value) than the conventional method.

To show clearly the variation of the measured values caused by air-blowing just before the measurement, for the case where the alkaline phosphatase is added, the calculation results of the present invention are shown in (A) and (B) in FIG. 8, and the calculation results of the conventional method, as (a) and (b) in FIG. 8; and for the case where the alkaline phosphatase is not added the calculation results of the present invention are shown in (C) and (D) in FIG. 8, and the calculation results of the conventional method, as (c) and (d) in FIG. 9. From these Figs., the calculation results are greatly disturbed in the conventional method (a to d) at the point of time of air-blowing, while, the calculation results of the present invention (A to D) are not affected such disturbance.

As described above, the method of assay of enzymatic activity and the apparatus therefor of the present invention are advantageous in that highly precise measurement is made possible with extremely little error caused by bubbles in the sample and meniscus of the sample in the cases where highly precise assay of enzymatic activity is required such as in enzyme labeled immunoassay and enzyme labeled DNA hybridization.

The method of assay of enzymatic activity and the apparatus therefor are also advantageous in that the substrate dispensing means, the agitation means for enzymatic reaction, and other means which had to be designed and handled carefully to decrease the measurement error in automated apparatuses for enzyme labeled immunoassay and enzyme labeled DNA hybridization can be simply constructed.

In an example of a conventional type of measuring apparatus, the measured fluorescence values are corrected by a sensor which detects the excitation-light intensity in consideration of deterioration with time of the lamp to emit the exciting light: for example, the correction being such that the detected fluorescence value is divided by emitted light intensity. In such a system, variation of light flux introduced to the sample container caused by variation of the relative position of the sample container to the lamp cannot be corrected, even though the deterioration with time of the intensity of the light emitted by the lamp can be corrected. On the contrary in the present invention, the measurement value is derived as the ratio of two fluorescence intensities at one point of time, so that the intensity of the light source does not directly affect the measurement results, and the measurement precision is greatly improved advantageously.

As described above, in the present invention, influence of external disturbance is excluded, and high sensitivity of the measurement can be realized.

What is claimed is:

1. A method of assay of enzymatic activity, comprising projecting monochromatic excitation light to a sample containing an enzyme, a substrate which forms a product by action of the enzyme, and a reference substance which is insensitive to the action of the enzyme but emits fluorescence; obtaining a first measured value of fluorescence intensity of the sample at a first wavelength region which includes fluorescence emitted by at least one of the substrate and the product; obtaining a second measured value of fluorescence intensity at a second wavelength region which is different from the first wavelength region and includes fluorescence emitted by the reference substance; and determining the enzymatic activity from a rate of change of a ratio of the first measured value to the second measured value.

2. The method according to claim 1, wherein said reference substance has a fluorescence peak wavelength at least 50 nm departed from a fluorescence peak wavelength of at least one of the substrate and the product.

3. The method according to claim 1, wherein the excitation light is in a wavelength region of light in which the light excites at least one of the substrate and the product, and the reference substance; the first measured value is obtained at a wavelength region of fluorescence emitted by at least one of the substrate and the product; and the second measured value is obtained at a wavelength region of fluorescence emitted mainly by the reference substance and substantially not including the fluorescence emitted by at least one of the substrate and the product.

4. The method according to claim 1, wherein the enzyme activity is assayed from the rate of change relative to time of a ratio of the first measured value to the second measured value.

5. A method of assay of enzymatic activity, comprising projecting monochromatic excitation light to a sample containing an enzyme, a substrate which forms a product by action of the enzyme, and a reference substance which is insensitive to the action of the enzyme but emits fluorescence; obtaining a first measured value of fluorescence intensity of the sample at a first wavelength region which includes fluorescence emitted by at least one of the substrate and the product; obtaining a second measured value of fluorescence intensity at a second wavelength region which is different from the first wavelength region and includes fluorescence emitted by the reference substance; and determining the enzymatic activity from a rate of change of a ratio of the first measured value to the second measured value, wherein the enzyme activity is assayed from the rate of change relative to time of ratio of the first measured value to the second measured value.

6. The method according to claim 5, wherein said reference substance has a fluorescence peak wavelength at least 50 nm departed from a fluorescence peak wavelength of at least one of the substrate and the product.

7. The method according to claim 6, wherein the excitation light is in a wavelength region of light in which the light excites at least one of the substrate and the product, and the reference substance; the first measured value is obtained at a wavelength region of fluorescence emitted by one or both of the substrate and the product; and the second measured value is obtained at a wavelength region fluorescence emitted mainly by the reference substance and substantially not including the fluorescence emitted by the substrate and/or the product.

* * * * *